US011331104B2

(12) United States Patent
Inouye et al.

(10) Patent No.: US 11,331,104 B2
(45) Date of Patent: May 17, 2022

(54) OCCLUSIVE SEALING SENSOR SYSTEM

(71) Applicant: BOSTON SCIENTIFIC SCIMED, INC., Maple Grove, MN (US)

(72) Inventors: Joshua Mark Inouye, Maple Grove, MN (US); Alex Pflugfelder, Excelsior, MN (US); Brian T. Berg, Saint Paul, MN (US); David John Onushko, Maple Grove, MN (US); James M. Anderson, Corcoran, MN (US); Markus Petteri Lohi, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 16/400,750

(22) Filed: May 1, 2019

(65) Prior Publication Data
US 2019/0336135 A1   Nov. 7, 2019

Related U.S. Application Data

(60) Provisional application No. 62/665,830, filed on May 2, 2018.

(51) Int. Cl.
*A61B 17/12* (2006.01)
*A61B 5/00* (2006.01)
(Continued)

(52) U.S. Cl.
CPC .... *A61B 17/12122* (2013.01); *A61B 5/02055* (2013.01); *A61B 5/07* (2013.01);
(Continued)

(58) Field of Classification Search
CPC ....... A61B 5/0215; A61B 5/024; A61B 5/026; A61B 17/0057; A61B 17/12022;
(Continued)

(56) References Cited

U.S. PATENT DOCUMENTS 1,782,830 A   6/1876  French
1,967,318 A  10/1931  Monahan
(Continued)

FOREIGN PATENT DOCUMENTS

CN   106859722 A   6/2017
WO      9313712 A1   7/1993
(Continued)

OTHER PUBLICATIONS

PCT Search Report from co-pending Application PCT/US02/33808 dated May 20, 2003.
(Continued)

*Primary Examiner* — Tan-Uyen T Ho
*Assistant Examiner* — Bridget E. Rabaglia
(74) *Attorney, Agent, or Firm* — Seager, Tufte & Wickhem LLP

(57) ABSTRACT

An example system for detecting leakage around an occlusive implant disposed in the left atrial appendage includes an elongate shaft having a port disposed at a distal end region thereof and a first sensor disposed adjacent the elongate shaft. The elongate shaft is configured to be positioned adjacent the occlusive implant such that the first sensor is positioned on a first side of the occlusive implant and the port is positioned on a second side of the occlusive implant. Further, the first sensor is configured to measure a first parameter and the first parameter is utilized to determine a fluid leak between the occlusive implant and a tissue wall defining the left atrial appendage.

15 Claims, 9 Drawing Sheets

(51) Int. Cl.
  *A61B 5/026* (2006.01)
  *A61B 17/00* (2006.01)
  *A61B 5/0205* (2006.01)
  *A61B 5/07* (2006.01)
  *A61B 5/0215* (2006.01)

(52) U.S. Cl.
  CPC ............ *A61B 5/4851* (2013.01); *A61B 5/686* (2013.01); *A61B 5/6852* (2013.01); *A61B 17/12031* (2013.01); *A61B 5/026* (2013.01); *A61B 5/0215* (2013.01); *A61B 2017/00004* (2013.01); *A61B 2017/00632* (2013.01); *A61B 2217/005* (2013.01); *A61B 2217/007* (2013.01)

(58) Field of Classification Search
  CPC ........ A61B 17/12109; A61B 17/12113; A61B 2017/00575; A61B 17/12031
  See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |

(56) References Cited

U.S. PATENT DOCUMENTS

| | | | |
|---|---|---|---|
| 5,928,260 A | 7/1999 | Chin et al. | |
| 5,935,145 A | 8/1999 | Villar et al. | |
| 5,935,147 A | 8/1999 | Kensey et al. | |
| 5,935,148 A | 8/1999 | Villar et al. | |
| 5,941,249 A | 8/1999 | Maynard | |
| 5,944,738 A | 8/1999 | Amplatz et al. | |
| 5,947,997 A | 9/1999 | Pavcnik et al. | |
| 5,951,589 A | 9/1999 | Epstein et al. | |
| 5,951,599 A | 9/1999 | McCrory | |
| 5,954,694 A | 9/1999 | Sunseri | |
| 5,957,940 A | 9/1999 | Tanner et al. | |
| 5,961,545 A | 10/1999 | Lentz et al. | |
| 5,976,174 A | 11/1999 | Ruiz | |
| 5,980,514 A | 11/1999 | Kupiecki et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,993,483 A | 11/1999 | Gianotti | |
| 5,997,557 A | 12/1999 | Barbut et al. | |
| 6,004,348 A | 12/1999 | Banas et al. | |
| 6,007,523 A | 12/1999 | Mangosong | |
| 6,007,557 A | 12/1999 | Ambrisco et al. | |
| 6,010,517 A | 1/2000 | Baccaro | |
| 6,010,522 A | 1/2000 | Barbut et al. | |
| 6,013,093 A | 1/2000 | Nott et al. | |
| 6,024,754 A | 2/2000 | Engelson | |
| 6,024,755 A | 2/2000 | Addis | |
| 6,024,756 A | 2/2000 | Huebsch et al. | |
| 6,027,520 A | 2/2000 | Tsugita et al. | |
| 6,033,420 A | 3/2000 | Hahnen | |
| 6,042,598 A | 3/2000 | Tsugita et al. | |
| 6,048,331 A | 4/2000 | Tsugita et al. | |
| 6,051,014 A | 4/2000 | Jang | |
| 6,051,015 A | 4/2000 | Maahs | |
| 6,056,720 A | 5/2000 | Morse | |
| 6,063,070 A | 5/2000 | Eder | |
| 6,068,621 A | 5/2000 | Balceta et al. | |
| 6,074,357 A | 6/2000 | Kaganov et al. | |
| 6,076,012 A | 6/2000 | Swanson et al. | |
| 6,079,414 A | 6/2000 | Roth | |
| 6,080,182 A | 6/2000 | Shaw et al. | |
| 6,080,183 A | 6/2000 | Tsugita et al. | |
| 6,083,239 A | 7/2000 | Addis | |
| 6,096,053 A | 8/2000 | Bates | |
| 6,110,243 A | 8/2000 | Wnenchak et al. | |
| 6,124,523 A | 9/2000 | Banas et al. | |
| 6,132,438 A | 10/2000 | Fleischman et al. | |
| 6,135,991 A | 10/2000 | Muni et al. | |
| 6,136,016 A | 10/2000 | Barbut et al. | |
| 6,139,527 A | 10/2000 | Laufer et al. | |
| 6,139,573 A | 10/2000 | Sogard et al. | |
| 6,152,144 A | 11/2000 | Lesh et al. | |
| 6,156,055 A | 12/2000 | Ravenscroft | |
| 6,161,543 A | 12/2000 | Cox et al. | |
| 6,171,329 B1 | 1/2001 | Shaw et al. | |
| 6,179,859 B1 | 1/2001 | Bates et al. | |
| 6,214,029 B1 | 4/2001 | Thill et al. | |
| 6,231,561 B1 | 5/2001 | Frazier et al. | |
| 6,231,589 B1 | 5/2001 | Wessman et al. | |
| 6,251,122 B1 | 6/2001 | Tsukernik | |
| 6,258,115 B1 | 7/2001 | Dubrul | |
| 6,270,490 B1 | 8/2001 | Hahnen | |
| 6,277,138 B1 | 8/2001 | Levinson et al. | |
| 6,290,674 B1 | 9/2001 | Roue et al. | |
| 6,319,251 B1 | 11/2001 | Tu et al. | |
| 6,328,727 B1 | 12/2001 | Frazier et al. | |
| 6,342,062 B1 | 1/2002 | Suon et al. | |
| 6,346,116 B1 | 2/2002 | Brooks et al. | |
| 6,364,895 B1 | 4/2002 | Greenhalgh | |
| 6,368,338 B1 | 4/2002 | Knya et al. | |
| 6,371,971 B1 | 4/2002 | Tsugita et al. | |
| 6,375,670 B1 | 4/2002 | Greenhalgh | |
| 6,391,044 B1 | 5/2002 | Yadav et al. | |
| 6,402,746 B1 | 6/2002 | Whayne et al. | |
| 6,419,669 B1 | 7/2002 | Frazier et al. | |
| 6,440,152 B1 | 8/2002 | Gainor et al. | |
| 6,443,972 B1 | 9/2002 | Bosma et al. | |
| 6,447,530 B1 | 9/2002 | Ostrovsky et al. | |
| 6,468,291 B2 | 10/2002 | Bates et al. | |
| 6,511,496 B1 | 1/2003 | Huter et al. | |
| 6,517,573 B1 | 2/2003 | Pollock et al. | |
| 6,547,760 B1 | 4/2003 | Samson et al. | |
| 6,551,303 B1 | 4/2003 | Van Tassel et al. | |
| 6,551,344 B2 | 4/2003 | Thill | |
| 6,558,405 B1 | 5/2003 | McInnes | |
| 6,562,058 B2 | 5/2003 | Seguin et al. | |
| 6,599,308 B2 | 7/2003 | Amplatz | |
| 6,652,555 B1 | 11/2003 | VanTassel et al. | |
| 6,652,556 B1 | 11/2003 | VanTassel et al. | |
| 6,689,150 B1 | 2/2004 | VanTassel et al. | |
| 6,730,108 B2 | 5/2004 | Van Tassel et al. | |
| 6,837,901 B2 | 1/2005 | Rabkin et al. | |
| 6,855,153 B2 | 2/2005 | Saadat | |
| 6,949,113 B2 | 9/2005 | Van Tassel et al. | |
| 6,994,092 B2 | 2/2006 | van der Burg et al. | |
| 7,011,671 B2 | 3/2006 | Welch | |
| 7,044,134 B2 | 5/2006 | Khairkhahan et al. | |
| 7,128,073 B1 | 10/2006 | van der Burg et al. | |
| 9,314,584 B1* | 4/2016 | Riley | A61B 5/743 |
| 2001/0034537 A1 | 10/2001 | Shaw et al. | |
| 2002/0022860 A1 | 2/2002 | Borillo et al. | |
| 2002/0035374 A1 | 3/2002 | Borillo et al. | |
| 2002/0062133 A1 | 5/2002 | Gilson et al. | |
| 2002/0138094 A1 | 9/2002 | Borillo et al. | |
| 2002/0138097 A1 | 9/2002 | Ostrovsky et al. | |
| 2003/0023266 A1 | 1/2003 | Borillo et al. | |
| 2003/0057156 A1 | 3/2003 | Peterson et al. | |
| 2003/0181942 A1 | 9/2003 | Sutton et al. | |
| 2003/0220667 A1 | 11/2003 | van der Burg et al. | |
| 2004/0098031 A1 | 5/2004 | van der Burg et al. | |
| 2004/0215230 A1 | 10/2004 | Frazier et al. | |
| 2005/0004652 A1 | 1/2005 | van der Burg et al. | |
| 2005/0113861 A1 | 5/2005 | Corcoran et al. | |
| 2005/0203568 A1 | 9/2005 | Burg et al. | |
| 2008/0033241 A1 | 2/2008 | Peh et al. | |
| 2012/0172731 A1 | 7/2012 | Smith | |
| 2013/0345574 A1* | 12/2013 | Davies | A61B 5/103 600/486 |
| 2014/0100596 A1 | 4/2014 | Rudman et al. | |
| 2014/0180239 A1 | 6/2014 | Mittermeyer et al. | |
| 2014/0323887 A1 | 10/2014 | Anderson et al. | |
| 2015/0119724 A1 | 4/2015 | Weber et al. | |
| 2015/0196300 A1 | 7/2015 | Tischler et al. | |
| 2016/0106437 A1 | 4/2016 | Van Der Burg et al. | |
| 2016/0310148 A1* | 10/2016 | Allen | A61B 17/1204 |
| 2020/0107836 A1* | 4/2020 | O'Halloran | A61B 17/12136 |
| 2020/0383688 A1* | 12/2020 | Olson | A61B 5/4839 |

FOREIGN PATENT DOCUMENTS

| | | |
|---|---|---|
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 0817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |

(56) References Cited

FOREIGN PATENT DOCUMENTS

WO         03032818 A2    4/2003
WO     2018187732 A1   10/2018

OTHER PUBLICATIONS

PCT Search Report from PCT/US99/26325 dated Feb. 15, 2000.
Cragg et al; "Nonsurgical Placement of Arterial Endoprosthesis: A New Technique Using Nitinol Wire," Radiology vol. 147, No. 1 pp. 261-263, Apr. 1983.
Cragg et al; "A New Percutaneous Vena Cava Filter", ALJ, 141: 601-604, Sep. 1983.
Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; Nonsurgical Closure of Patent Ductus Arteriosus: Clinical Application of the Rashkind PDA Occluder System, Circulation 75, No. 3, 583-592—1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.
International Search Report and Written Opinion for Application No. PCT/US2019/030220, 11 pages, dated Aug. 2, 2019.

\* cited by examiner

OCCLUSIVE SEALING SENSOR SYSTEM

CROSS-REFERENCE TO RELATED APPLICATIONS

This application claims the benefit of priority under 35 U.S.C. § 119 to U.S. Provisional Application Ser. No. 62/665,830, filed May 2, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. In some instances, improper placement of the medical device in the left atrial appendage may result in an insufficient seal between the medical device and the tissue wall defining the left atrial appendage. A continuing need exists for improved medical devices and methods to detect leakage around an occlusive implant disposed in the left atrial appendage.

SUMMARY

An example system for detecting leakage around an occlusive implant disposed in the left atrial appendage includes an elongate shaft having a port disposed at a distal end region thereof and a first sensor disposed adjacent the elongate shaft. The elongate shaft is configured to be positioned adjacent the occlusive implant such that the first sensor is positioned on a first side of the occlusive implant and the port is positioned on a second side of the occlusive implant. Further, the first sensor is configured to measure a first parameter and the first parameter is utilized to determine a fluid leak between the occlusive implant and a tissue wall defining the left atrial appendage.

In addition or alternatively, wherein the first parameter includes at least one of a fluid flowrate, a fluid pressure and a fluid temperature.

In addition or alternatively, wherein the elongate shaft is configured to inject fluid into the left atrial appendage.

In addition or alternatively, wherein the elongate shaft is configured to vacuum fluid out of the left atrial appendage.

In addition or alternatively, further comprising a core wire coupled to the occlusive implant, and wherein the first sensor is disposed on the core wire.

In addition or alternatively, further comprising a second sensor disposed on a hub of the occlusive implant.

In addition or alternatively, wherein the first sensor is attached to the elongate shaft.

In addition or alternatively, further comprising a second sensor attached to the elongate shaft on the second side of the implant.

In addition or alternatively, wherein the elongate shaft includes a core wire and a second sensor, wherein the core wire is coupled to the occlusive implant, and wherein the first sensor is disposed on the core wire on the first side of the implant, and wherein the second sensor is disposed on the core wire on the second side of the implant.

In addition or alternatively, further comprising a membrane coupled to the first side of the occlusive implant.

In addition or alternatively, wherein the membrane is configured to prevent fluid from passing therethrough.

In addition or alternatively, wherein the membrane is retractable.

In addition or alternatively, wherein the membrane includes an absorbable material.

In addition or alternatively, wherein the sensor is wireless.

Another system for detecting leakage around an occlusive implant disposed in the left atrial appendage includes:

an elongate shaft having a first sensor disposed on a first portion thereof and a second sensor disposed along a second portion thereof;

wherein the elongate shaft is configured to be positioned adjacent the occlusive implant such that the first sensor is positioned on a first side of the occlusive implant, and wherein the second sensor is positioned on a second side of the occlusive implant;

wherein the first sensor is configured to measure a first parameter;

wherein the second sensor is configured to measure a second parameter;

wherein the first parameter is compared to the second parameter to determine a fluid leak between the occlusive implant and a tissue wall defining the left atrial appendage.

In addition or alternatively, wherein the first parameter, the second parameter or both the first parameter and the second parameter include at least one of a fluid flowrate, a fluid pressure and a fluid temperature.

In addition or alternatively, wherein the elongate shaft is coupled to a hub on the occlusive implant.

In addition or alternatively, further comprising a core wire coupled to the occlusive implant.

In addition or alternatively, wherein the first sensor, the second sensor or both the first and second sensor are wireless.

A method for detecting leakage around an occlusive implant disposed in the left atrial appendage includes:

advancing an elongate shaft into the left atrial appendage, the elongate shaft including a first sensor disposed thereon and a port disposed at a distal end region thereof;

positioning the elongate shaft adjacent the occlusive implant such that the first sensor is positioned on a first side of the occlusive implant and the port is positioned on a second side of the occlusive implant;

measuring a first parameter with the first sensor;

utilizing the first parameter to determine a fluid leak between the occlusive implant and a tissue wall defining the left atrial appendage.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
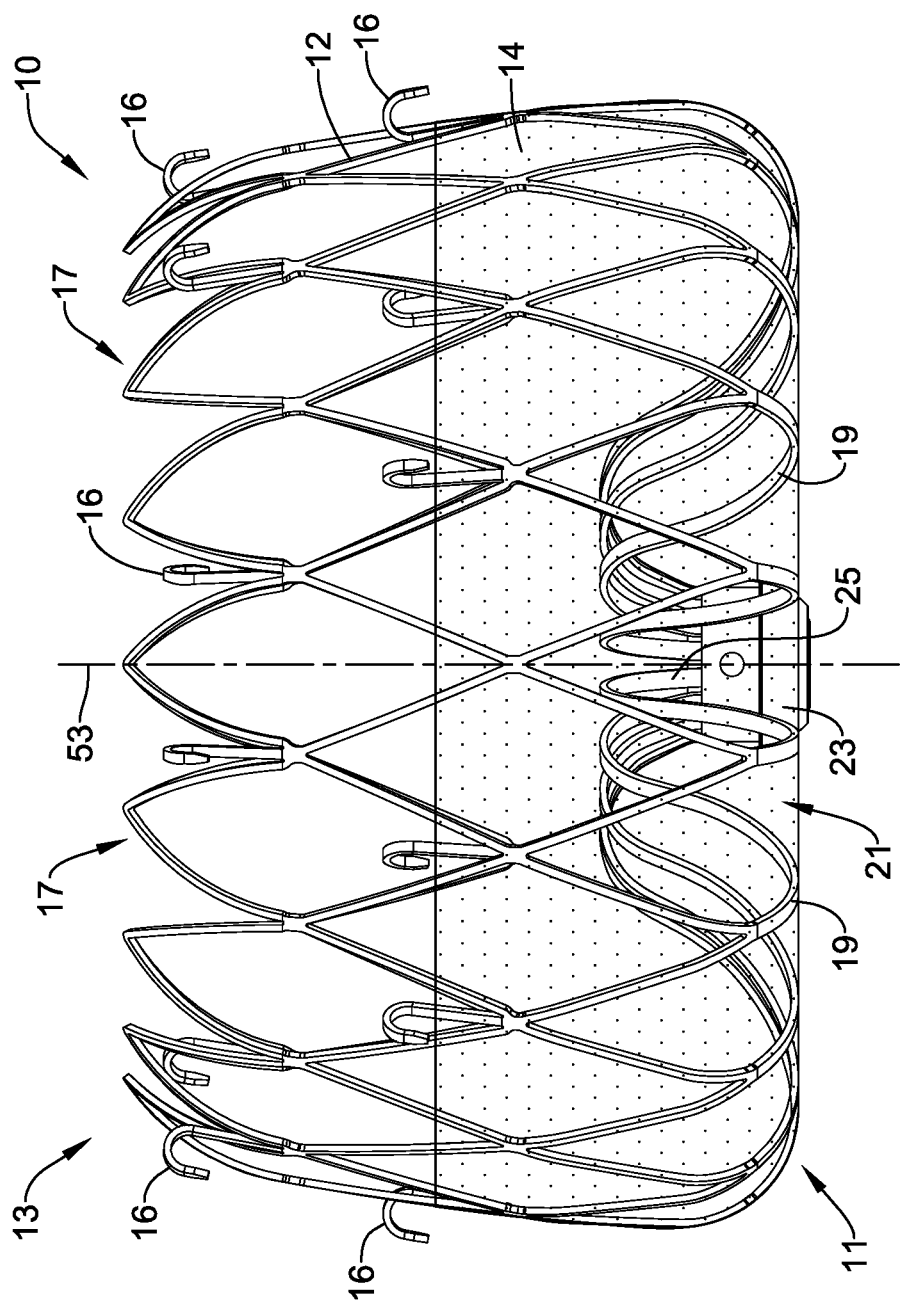
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thromboembolic material entering the blood stream from the left atrial appendage. However, in some instances one or more factors (e.g., improper placement, improper sizing, irregular-shaped left atrial appendage, etc.) may result in improper sealing of the occlusive implant along the tissue wall defining the left atrial appendage. Example medical devices and/or occlusive implants which detect leakage around an occlusive implant disposed in the left atrial appendage are disclosed. FIG. 1 illustrates an example occlusive implant 10. The occlusive implant 10 may include an expandable framework 12. The expandable framework 12 may include a proximal end region 11 and a distal end region 13. FIG. 1 further illustrates that the expandable framework 12 may include one or more projections 17 extending in a proximal-to-distal direction. In some instances (such as that shown in FIG. 1), plurality of projections 17 may extend circumferentially around a longitudinal axis 53 of the expandable framework 12. In other words, in some examples the projections 17 may resemble the peaks of a "crown" extending circumferentially around a longitudinal axis 53 of the expandable framework 12. While the above discussion (and the illustration shown in FIG. 1), shows a plurality of projections 17, it is contemplated that the occlusive implant 10 may include 1, 2, 3, 4, 5, 6, 7, 8, 9, 10, 11, 12 or more individual projections 17 disposed in a variety of arrangements along the expandable framework 12.

Additionally, FIG. 1 illustrates that the proximal end region 11 of the expandable framework 12 may include a plurality of support members 19 extending circumferentially around the longitudinal axis 53 of the expandable framework 12. FIG. 1 illustrates that that plurality of support members 19 may include one or more curved portions which are shaped such that they define a "recess" 21 extending distally into the expandable framework 12. As illustrated in FIG. 1, the recess 21 may extend circumferentially around the longitudinal axis 53. Further, FIG. 1 illustrates that each of the plurality of support members 19 may include a first end 25 which is attached to a central hub 23. It can be appreciated that the central hub 23 may be aligned along the longitudinal axis 53 of the expandable framework 12. FIG. 1 illustrates that the hub 23 may be positioned such that it lies within the recess 21 defined by the plurality of support members 19.

The occlusive implant 10 may also include a first occlusive member 14 disposed on, disposed over, disposed about, or covering at least a portion of the expandable framework 12. In some embodiments, the first occlusive member 14 may be disposed on, disposed over, disposed about or cover at least a portion of an outer (or outwardly-facing) surface of the expandable framework 12. FIG. 1 further illustrates that the first occlusive member 14 may extend only partially along the longitudinal extent of the expandable framework 12. However, this is not intended to be limiting. Rather, the first occlusive member 14 may extend along the longitudinal extent of the expandable framework 12 to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelialization after implantation, thereby effectively removing the left atrial appendage from the patient's circulatory system. Some suitable, but non-limiting, examples of materials for the occlusive member 14 are discussed below.

FIG. 1 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 1. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, welding, etc. Other means and/or methods are also contemplated.

As illustrated in FIG. 1, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

Figure 2:
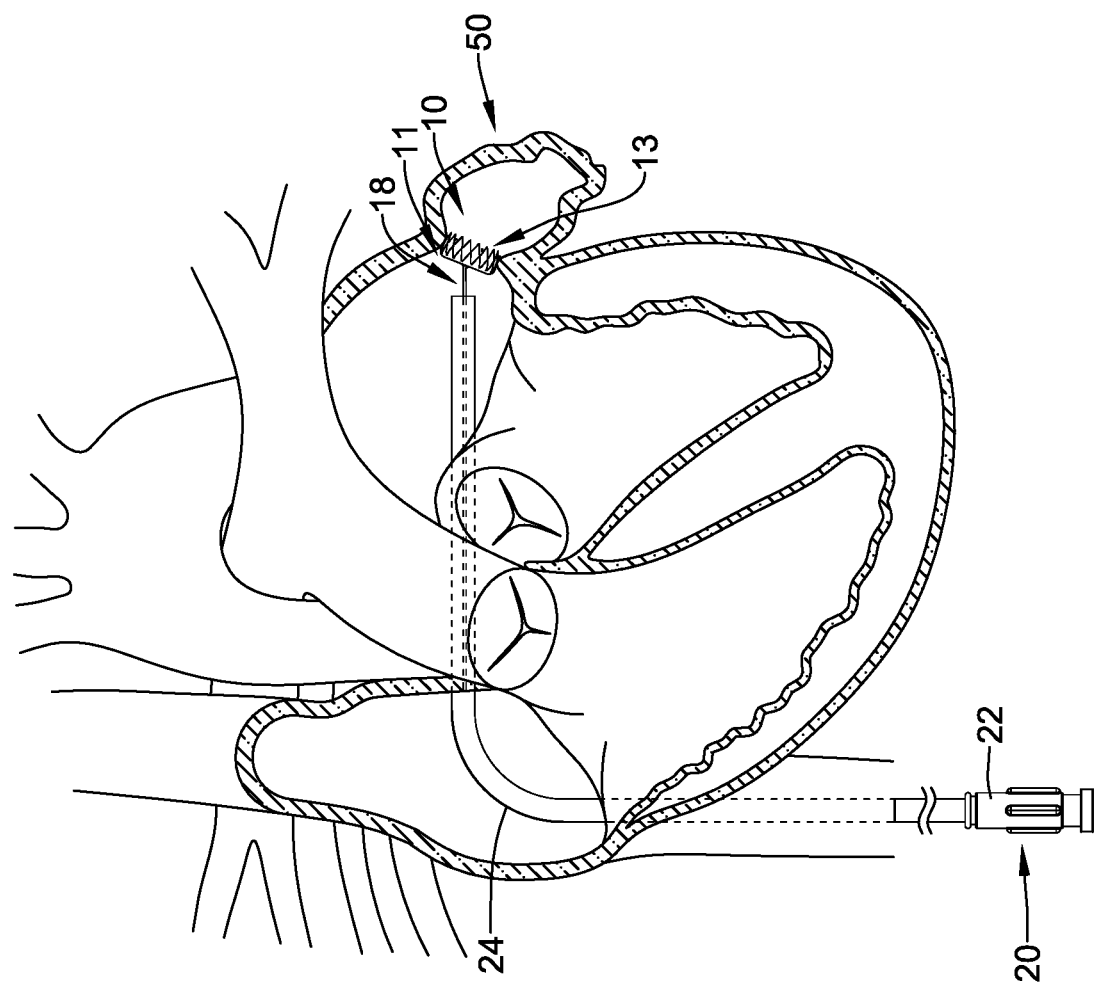
FIG. 2 illustrates an example occlusive implant positioned in the heart.

FIG. 2 illustrates an example occlusive implant 10 positioned within the left atrial appendage 50. FIG. 2 further illustrates that the occlusive implant 10 may be inserted and advanced through a body lumen via an occlusive implant delivery system 20. In some instances, an occlusive implant delivery system 20 may include a delivery catheter 24 which is guided toward the left atrium via various chambers and lumens of the heart (e.g., the inferior vena cava, superior vena cava, the right atrium, etc.) to a position adjacent the left atrial appendage 50. In some examples, the occlusive implant 10 may be configured to shift between a collapsed configuration and an expanded configuration. For example, in some instances, the occlusive implant 10 may be in a collapsed configuration during delivery via an occlusion implant delivery system, whereby the occlusive implant 10 expands to an expanded configuration once deployed from the occlusion implant delivery system 20.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. In some examples, the core wire 18 may be a solid member. However, in other examples the core wire 18 may include a lumen (it is noted that the lumen of the core wire 18 is not shown in FIG. 2). As will be discussed below, in some examples the core wire 18 may be designed such that a fluid may be passed through a lumen extending therewithin. Further, a proximal end 11 of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

FIG. 2 further illustrates that the distal end region 13 of the expandable framework 12 may extend farther into the left atrial appendage 50 as compared to the proximal end region 11 of the expandable framework 12. It can be appreciated that as the expandable framework 12 is advanced into the left atrial appendage 50, the distal end region 13 may engage with tissue defining the left atrial appendage 50. In other words, in some examples the distal end region 13 may be considered the "leading" region of the expandable framework 12 as it enters into the left atrial appendage 50. However, this is not intended to be limiting. Rather, in some examples the proximal end region 11 may be considered the "leading" region of the expandable framework 12 as it enters into the left atrial appendage 50.

Figure 3:
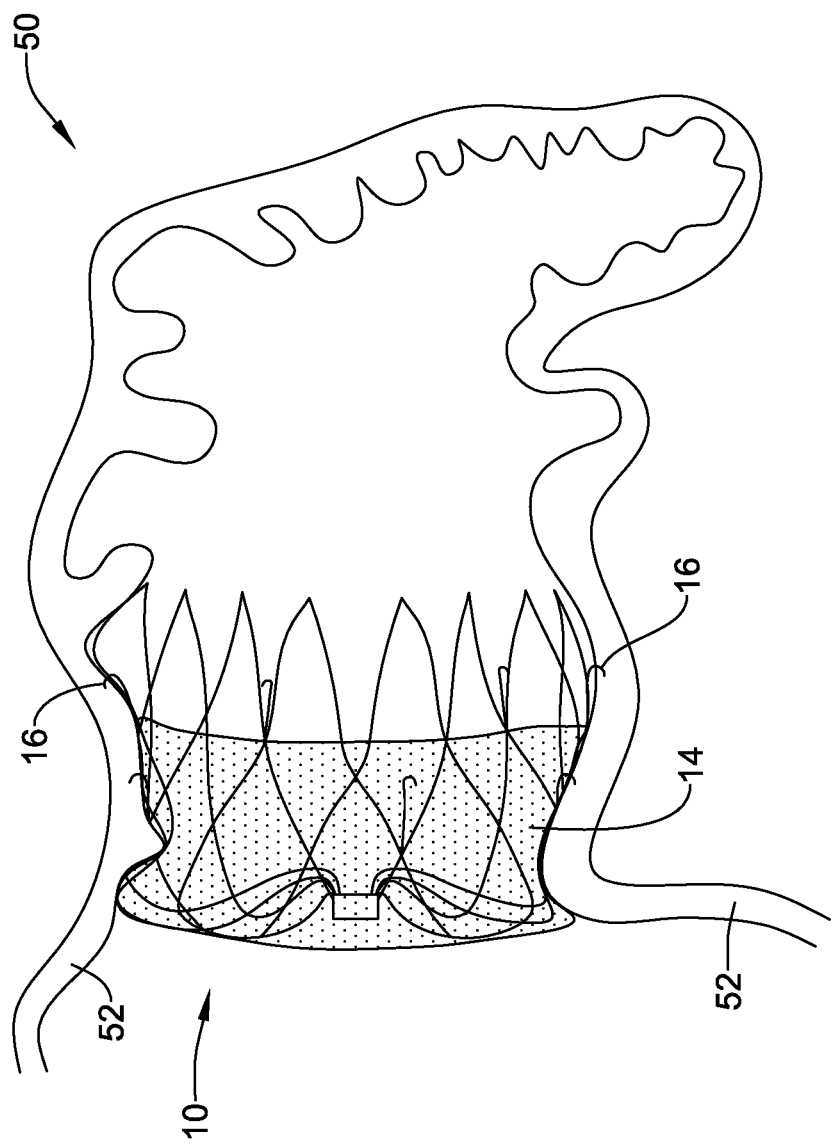
FIG. 3 illustrates an example occlusive implant positioned in the left atrial appendage.

FIG. 3 illustrates the example occlusive implant 10 positioned within the left atrial appendage 50. Additionally, FIG. 3 illustrates that the expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue 52 and/or lateral wall of the left atrial appendage. Additionally, FIG. 3 illustrates that the expandable framework 12 may be held fixed adjacent to the left atrial appendage by one or more anchoring members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant 10 within the left atrial appendage. Several example occlusion devices including various sealing features are disclosed below.

However, in some instances one or more factors (e.g., improper placement, improper sizing, irregular-shaped left atrial appendage, etc.) may result in improper sealing of the occlusive implant 10 along the tissue wall defining the left atrial appendage 50. For example, in some instances the occlusive implant 10 may not conform to the tissue around it, whereby a gap forms between the occlusive implant 10 and the tissue wall defining the left atrial appendage.

Figure 4:
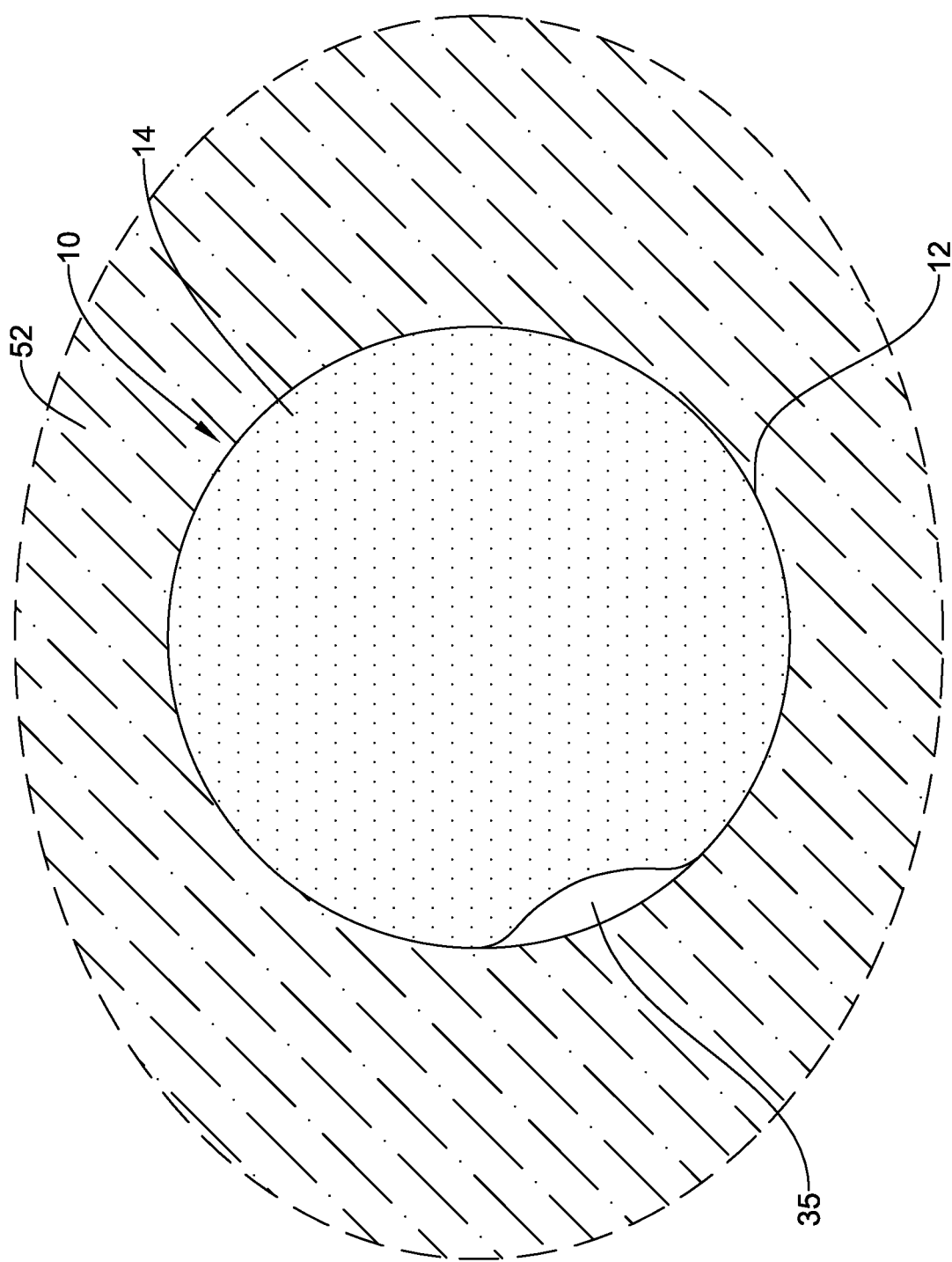
FIG. 4 illustrates an end view of an example occlusive implant positioned in the left atrial appendage.

For example, FIG. 4 illustrates the occlusive implant 10 positioned within the left atrial appendage 50 (described above). The positioning of the occlusive implant 10 shown in FIG. 4 is similar to that shown in FIG. 3, however, FIG. 4 illustrates an alternate view of the occlusive implant 10. In particular, FIG. 4 illustrates an end view of the occlusive implant 10 positioned in the left atrial appendage 50 (e.g., a view of the bottom of the occlusive device 10 looking inward at the left atrial appendage 50). FIG. 4 illustrates the occlusive member 14 spanning the proximal (e.g., left atrium facing) portion of the framework 12. Further, FIG. 4 illustrates that the occlusive member 14 may extend across the proximal portion of the framework 12 to a position where it contacts tissue 52 which is surrounding the left atrial appendage 50. It can be appreciated from FIG. 4 that the occlusive member 14 may extend circumferentially around the entire opening of the left atrial appendage. In other words, a portion of the occlusive member 14 may be positioned adjacent to the surrounding tissue 52 which is adjacent to the left atrial appendage (e.g., positioned around the circumference of the opening to the left atrial appendage 50).

However, while can be appreciated that the occlusive device 10 may be able to conform to the specific shape and/or geometry of a lateral wall of a left atrial appendage 50, FIG. 4 illustrates that in some instances a gap 35 may form between the occlusive implant 10 and the surrounding tissue 52 defining the left atrial appendage 50. In other words, the occlusive device 10 may not entirely fill and/or conform to the specific shape and/or geometry of a lateral wall of a left atrial appendage 50 when positioned adjacent thereto, resulting in a gap 35.

As discussed above, it may be desirable to detect leakage which may occur around an improperly sealed left occlusive implant. It can be appreciated that being able to identify leakage around an occlusive implant may allow a clinician to reposition the implant and seal off the leaking fluid. Alternatively, a clinician may opt to retrieve an occlusive implant which has been improperly positioned.

Figure 5:
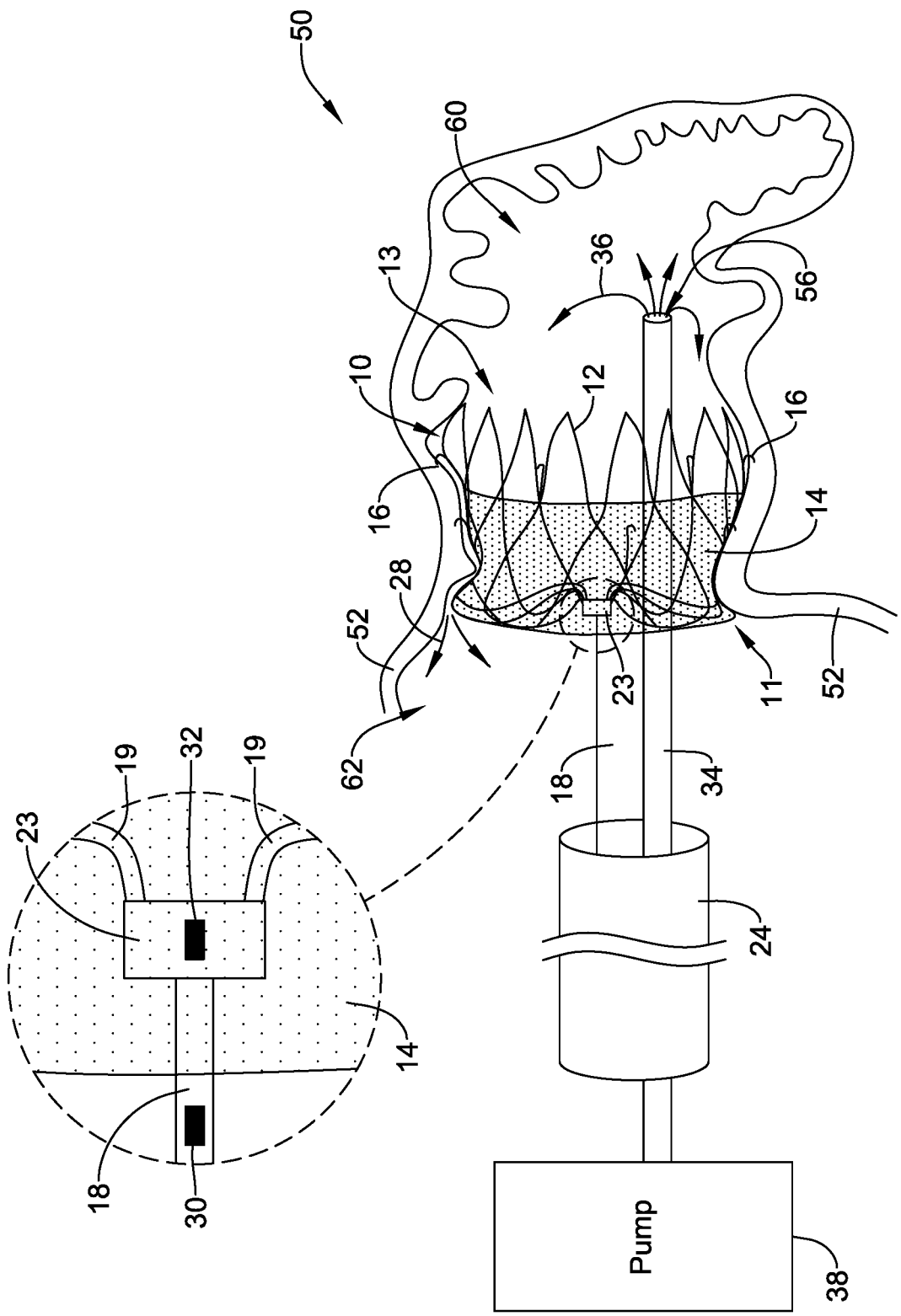
FIG. 5 illustrates a portion of an example occlusive member sensing system.

FIG. 5 illustrates an example system and methodology for detecting fluid leakage around an occlusive implant 10. FIG. 5 illustrates the example occlusive implant 10 (including the framework 12 and the occlusive member 14) positioned within the left atrial appendage 50. FIG. 5 further illustrates that the distal end region 13 of the occlusive implant 10 extending farther into the left atrial appendage 50 as compared to the proximal end region 11 of the occlusive implant 10. Additionally, FIG. 5 illustrates that the occlusive implant 10 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue 52 and/or lateral wall of the left atrial appendage 50. Additionally, FIG. 5 illustrates that the occlusive implant 10 may be held fixed adjacent to the left atrial appendage 50 by one or more anchoring members 16.

Additionally, FIG. 5 illustrates that the example occlusive implant 10 may be coupled to a core wire 18. As illustrated in the detailed view of FIG. 5, the core wire 18 may be attached to the occlusive implant 10 via the central the hub 23. Further, the detailed view of FIG. 5 illustrates the support members 19 of the framework 12 attached to the central hub 23. The detailed view of FIG. 5 further illustrates a first sensor 30 positioned along a portion of the core wire 18. Further, the detailed view of FIG. 5 further illustrates a second sensor 32 disposed along a portion of the central hub 23. It is noted that the examples described herein that include two sensors are not intended to be limiting. Rather, it is contemplated that any of the examples described herein may include more or less than two sensors. For example, the examples may include 1, 2, 3, 4, 5, 6 or more sensors.

Further, the arrangement of the first sensor 30 and the second sensor 32 shown in FIG. 5 (or any of the figures herein) is merely exemplary and not intended to be limiting. Rather, it is contemplated that the first sensor 30 and/or the second sensor 32 may be positioned and/or arranged along other portions of the core wire 18, the central hub 23, the framework 12 and/or the occlusive member 14. For example, it is contemplated that both the first sensor 30 and the second sensor 32 may each be positioned on the core wire 18. Additionally, it is contemplated that any of the sensors disclosed herein may be fully or partially embedded within any of the components (e.g., implants, core wires, catheters, expandable members, wires, etc.) described herein.

The first sensor 30 and/or the second sensor 32 may be designed to sense, measure, collect, record, etc. one or more parameters related to the flow of fluid (e.g., blood) adjacent to the occlusive implant 10 and/or the left atrial appendage 50. For example, the first sensor 30 and/or the second sensor 32 may be designed to sense, measure, collect and/or record fluid flowrates, fluid pressures, fluid temperature, etc. Any of the sensors described herein (including the first sensor 30 and/or the second sensor 32) may include flow rates sensors, pressure sensors (e.g., piezoelectric sensors, Fiber Bragg sensors, optical pressure sensors, passive pressure sensors, etc.), temperature sensors, etc. It is contemplated that any of the sensors described herein (including the first sensor 30 and/or the second sensor 32) may be able to sense, measure, collect and/or record a combination of different parameters (e.g., a combination of fluid flowrates, fluid pressures, fluid temperature, etc.).

Additionally, it is contemplated that the first sensor 30 and/or the second sensor 32 may be wired to a processor (not shown), whereby the processor may be designed to utilize the data sensed, measured and/or collected by the first sensor 30 and/or the second sensor 32 to calculate and/or compare one or more parameters (e.g., fluid flowrates, fluid pressures, fluid temperature, etc.). For example, it can be appreciated that in order to determine whether fluid is leaking around the occlusive implant 10 shown in FIG. 5, it may be desirable to measure and compare the flowrate of fluid on one side of the occlusive implant 10 to the flowrate of fluid on the opposite side of the occlusive implant 10.

For example, provided that the occlusive implant 10 was properly placed along the opening to the left atrial appendage 50 such that no gaps existed between the occlusive implant 10 and the surrounding tissue 52 (as described above), the occlusive member 14 may substantially prevent fluid from flowing out of the left atrial appendage 50 and into the left atrium. Accordingly, it can be appreciated that the fluid flux between a properly sealed left atrial appendage 50 and the left atrium may be approximately zero (as no fluid would be flowing out any gaps between the occlusive implant 10 and the surrounding tissue 52). It is noted that the area inside the left atrial appendage 50 is denoted by the reference numeral "60" in FIG. 5. The inside portion of the left atrial appendage 50 as contemplated herein may be defined as that portion of the left atrial appendage 50 bounded by the inner, concave surface of the occlusive implant 10. This is in contrast to the area "outside" the left atrial appendage 50 which is denoted by the reference numeral "62" in FIG. 5. Further, "outside" the left atrial appendage 50 as contemplated herein may be defined as that portion of the left atrium located outside the outer, convex surface of the occlusive implant 10. In some examples, the occlusive member 14 may define the boundary between a fluid positioned inside the left atrial appendage 50 and the left atrium.

If a gap exists between the occlusive implant 10 and the surrounding tissue 52, it can be appreciated that fluid may flow from inside the left atrial appendage 50 to a location within the left atrium. Accordingly, the presence of leakage around the occlusive implant 10 may be detected by measuring a first parameter (e.g., a first fluid flowrate, a first fluid pressure, etc.) outside of the occlusive implant 10 and comparing it a second parameter (e.g., a second fluid flowrate, a second fluid pressure, etc.) on the inside of the occlusive implant 10. The difference between the first parameter value and the second parameter value may not only provide an indication of the presence of fluid leakage around the occlusive implant 10, but may also provide an indication of the degree (e.g., volumetric flow rate) of fluid leaking around the occlusive implant 10.

To that end, in any of the examples disclosed herein, it may be beneficial to pump a fluid (e.g., saline) inside a deployed occlusive implant 10 in order to more easily detect a potential fluid leakage point through a gap between the occlusive implant 10 and the surrounding tissue 52. In some examples, the fluid may be pumped in a series of pulses (e.g., transient bolus injection). However, in other examples, the fluid may be pumped as a steady-state fluid flow. Further, or examples may include passive measurement of the blood pressure absent a pumping mechanism. FIG. 5 illustrates an example catheter 34 extending within a delivery catheter 24 (FIG. 5 also shows the core wire 18 extending within the delivery catheter 24). Further, the catheter 34 may include a distal end region, a proximal end region and a lumen extending therein. As shown in FIG. 5, the proximal end region of the catheter 34 may be coupled to a pump 38.

FIG. 5 further illustrates that the catheter 34 may extend through the occlusive implant 10 such that the distal end region of the catheter 34 may be positioned inside the left atrial appendage 50. Further, FIG. 5 illustrates that fluid 36 may be pumped through a distal port 56 of the catheter 34 into the inside 60 of the left atrial appendage 50. For illustrative purposes, FIG. 5 shows fluid 28 leaking from one side of the occlusive implant 10 (e.g., from the inside area 60) to the other side of the occlusive implant 10 (e.g., to an area 62 within the left atrium).

As described above, it can be appreciated that the first sensor 30 may be utilized to measure a first parameter (e.g., a first fluid flowrate, a first fluid pressure, etc.) on the outside of the occlusive implant 10, while the second sensor 32 may be utilized to measure a second parameter (e.g., a second fluid flowrate, a second fluid pressure, etc.) on the inside of the occlusive implant 10. As discussed above, comparison of the parameter measurements (or parameters calculated based upon the collected first parameter and the second parameter) may be utilized to determine the presence and extent of fluid leakage around the occlusive implant 10.

Additionally, it is contemplated that any of the sensors described herein may be positioned externally to the body. For example, in some instances it may be desirable to position one or more sensors adjacent to the pump 38 and/or any other structure located on the outside of a patient's body. Positioning one or more sensors outside of a patient's body may be beneficial because the complexity of the system may be reduced. Furthermore, externally-positioned sensors may be reused whereas sensors inside the body may be single-use (due to sterilization, for example).

Further, as described above, using parameters measured at the pump orifice or inside the pump (e.g., volumetric flowrate, pressure, etc.), a leak may be calculated without having sensors inside the body by any means. It is also noted that external sensor readings may be coupled with internal sensor readings. For example, the pump may measure flow rate externally while one or more pressures (or temperatures, etc.) may be measured internally on the implant or catheter.

Additionally, it can be appreciated that the parameters discussed above (e.g., fluid flowrate, volumetric flowrate, fluid pressure, etc.) may vary with time. Therefore, changes in the parameters over time may provide additional information regarding the effective seal provided by the occlusive implant 10. For example, if the pump flow rate is held constant and the observed (e.g., measured, sensed) pressure inside the left atrial appendage 50 rises quasi-steadily over several hear beats, it may imply that the occlusive implant is providing a substantially effective seal. However, in another example, if the pump flowrate is held constant and the pressure rises and then becomes quasi-constant, provided that rise is negligible, it may imply that the there is a substantial leak between the occlusive implant 10 and the surrounding tissue 52. However, if the rise is relatively large, it may imply that the occlusive implant is providing a substantially effective seal.

Figure 6:
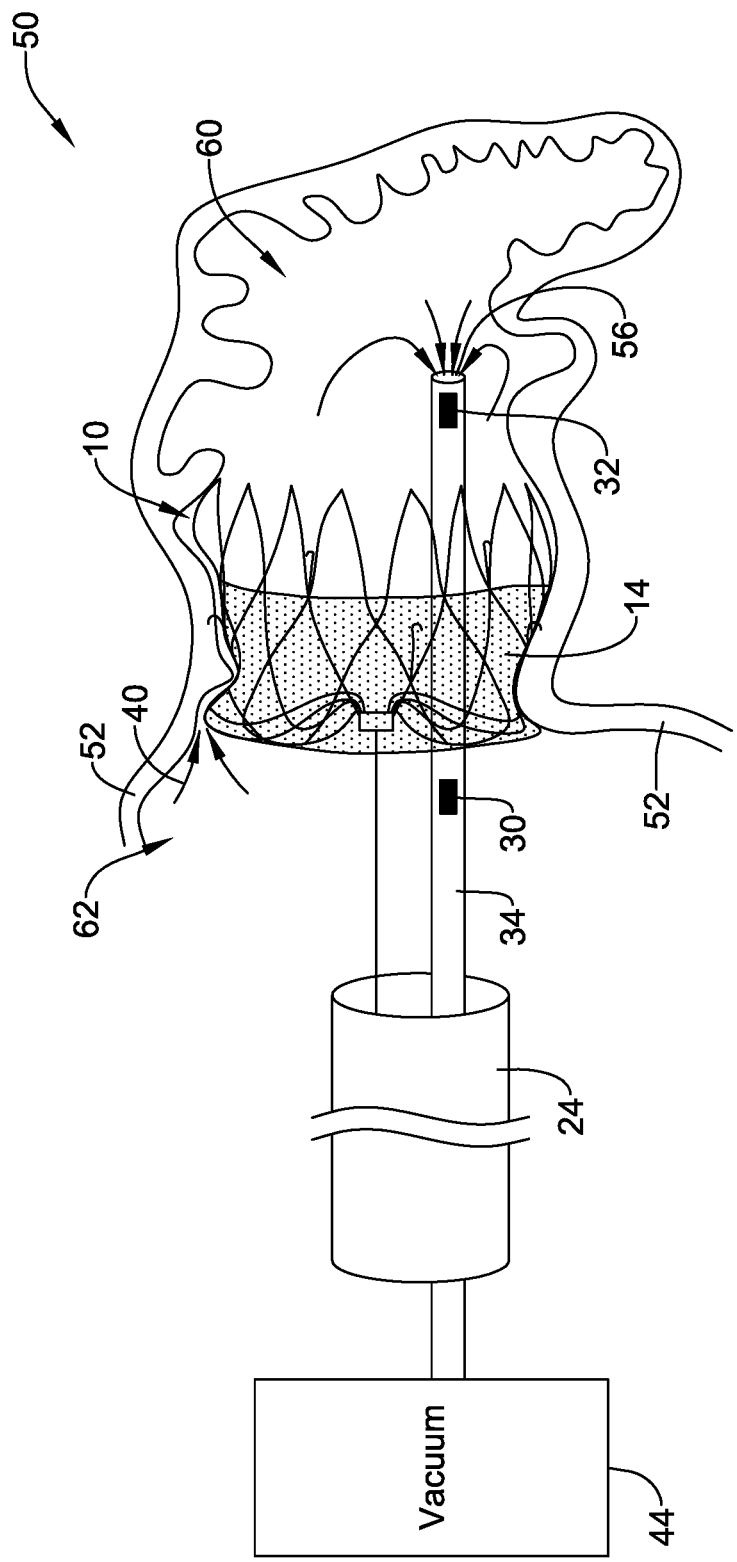
FIG. 6 illustrates a portion of another occlusive member sensing system.

FIG. 6 illustrates another example of a system and methodology to detect leakage around an example occlusive implant 10. FIG. 6 shows the occlusive implant 10 positioned within the opening of the left atrial appendage 50 similarly to that described above with respect to FIG. 5. For example, FIG. 6 illustrates that the catheter 34 may extend through the occlusive implant 10 such that the distal end region of the catheter 34 may be positioned inside the left atrial appendage 50. Additionally, FIG. 6 shows that in some examples, the first sensor 30 may be positioned along the catheter 34 at a location which is outside of the occlusive implant 10 and the second sensor 32 may be positioned along the distal end region of the catheter 34.

Further, FIG. 6 illustrates that the catheter 34 may be coupled to a vacuum 44. Accordingly, fluid 42 may be vacuumed into a distal port 56 of the catheter 34 from inside the left atrial appendage 50. The vacuuming of fluid into the catheter 34 from inside the left atrial appendage 50 may cause fluid to be pulled through gaps between the occlusive implant 10 and the surrounding tissue 52. For illustrative purposes, FIG. 6 shows fluid 40 leaking into the occlusive implant 10 (e.g., from the outside area 62) to the other side of the occlusive implant 10 (e.g., to an area 60 inside the occlusive implant 10). As discussed above, it can be appreciated that the first sensor 30 may be utilized to measure a first parameter (e.g., a first fluid flowrate, a first fluid pressure, etc.) on the outside of the occlusive implant 10, while the second sensor 32 may be utilized to measure a second parameter (e.g., a second fluid flowrate, a second fluid pressure, etc.) on the inside of the occlusive implant 10. As discussed above, comparison of the parameter measurements (or parameters calculated based upon the collected first parameter and the second parameter) may be utilized to determine the presence and extent of fluid leakage around the occlusive implant 10.

Figure 7:
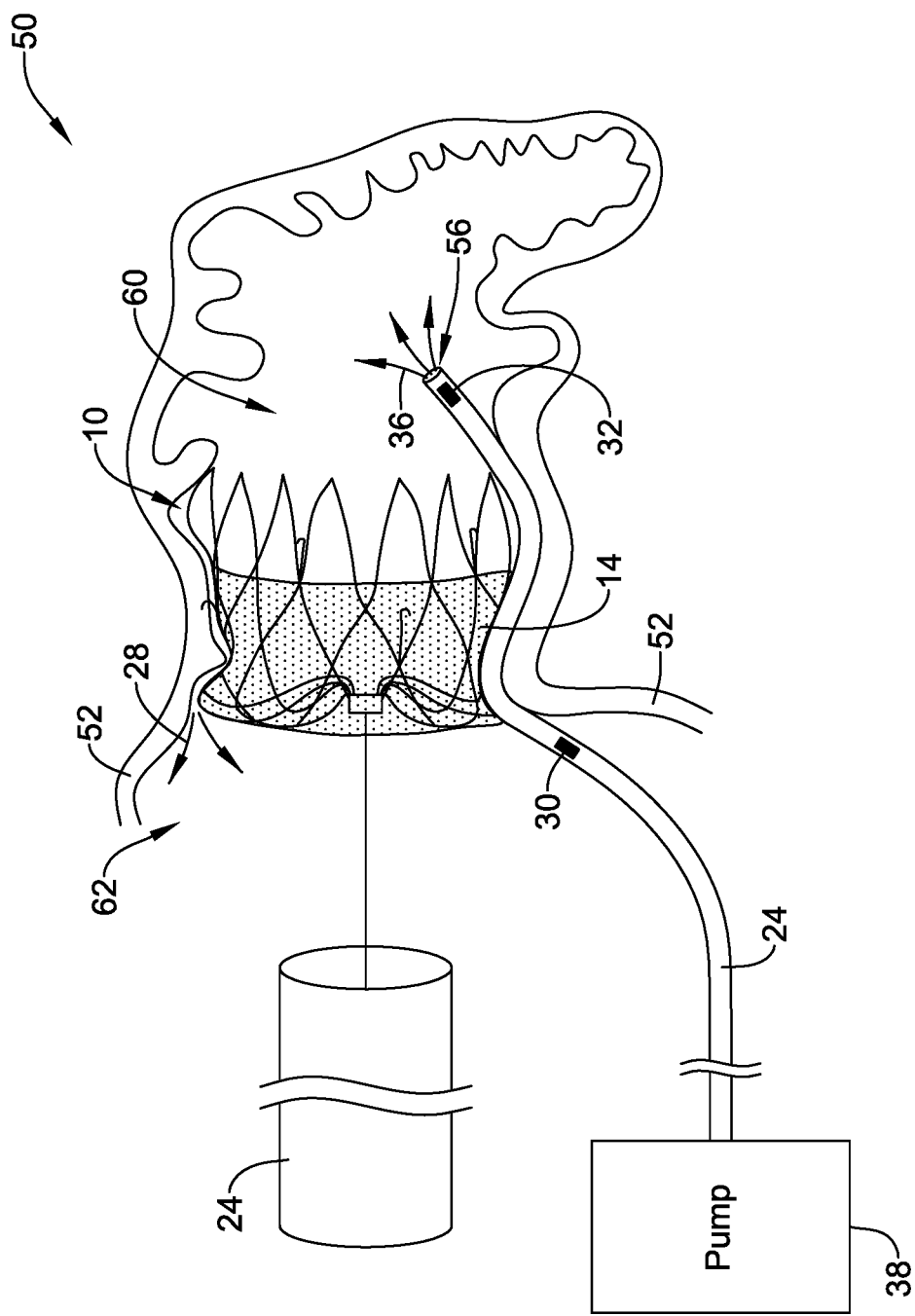
FIG. 7 illustrates a portion of another occlusive member sensing system.

FIG. 7 illustrates another example of a system and methodology to detect leakage around an example occlusive implant 10. FIG. 7 shows the occlusive implant 10 positioned within the opening of the left atrial appendage 50 similarly to that described above. However, FIG. 7 illustrates the catheter 34 may extend along occlusive implant 10 (e.g., between the occlusive implant 10 and the surrounding tissue 52), whereby the distal end region of the catheter 34 may be positioned inside the left atrial appendage 50. Additionally, FIG. 7 shows that in some examples, the first sensor 30 may be positioned along the catheter 34 at a location which is outside of the occlusive implant 10 and the second sensor 32 may be positioned along the distal end region of the catheter 34.

Further, FIG. 7 illustrates that the catheter 24 may be coupled to a pump 38. Accordingly, fluid 36 may be pumped through a distal port 56 of the catheter 34 into the inside 60 of the left atrial appendage 50. For illustrative purposes, FIG. 7 shows fluid 28 leaking from one side of the occlusive implant 10 (e.g., from the inside area 60) to the other side of the occlusive implant 10 (e.g., to an area 62 within the left atrium). As discussed above, it can be appreciated that the first sensor 30 may be utilized to measure a first parameter (e.g., a first fluid flowrate, a first fluid pressure, etc.) on the outside of the occlusive implant 10, while the second sensor 32 may be utilized to measure a second parameter (e.g., a second fluid flowrate, a second fluid pressure, etc.) on the inside of the occlusive implant 10. As discussed above, comparison of the parameter measurements (or parameters calculated based upon the collected first parameter and the second parameter) may be utilized to determine the presence and extent of fluid leakage around the occlusive implant 10.

Figure 8:
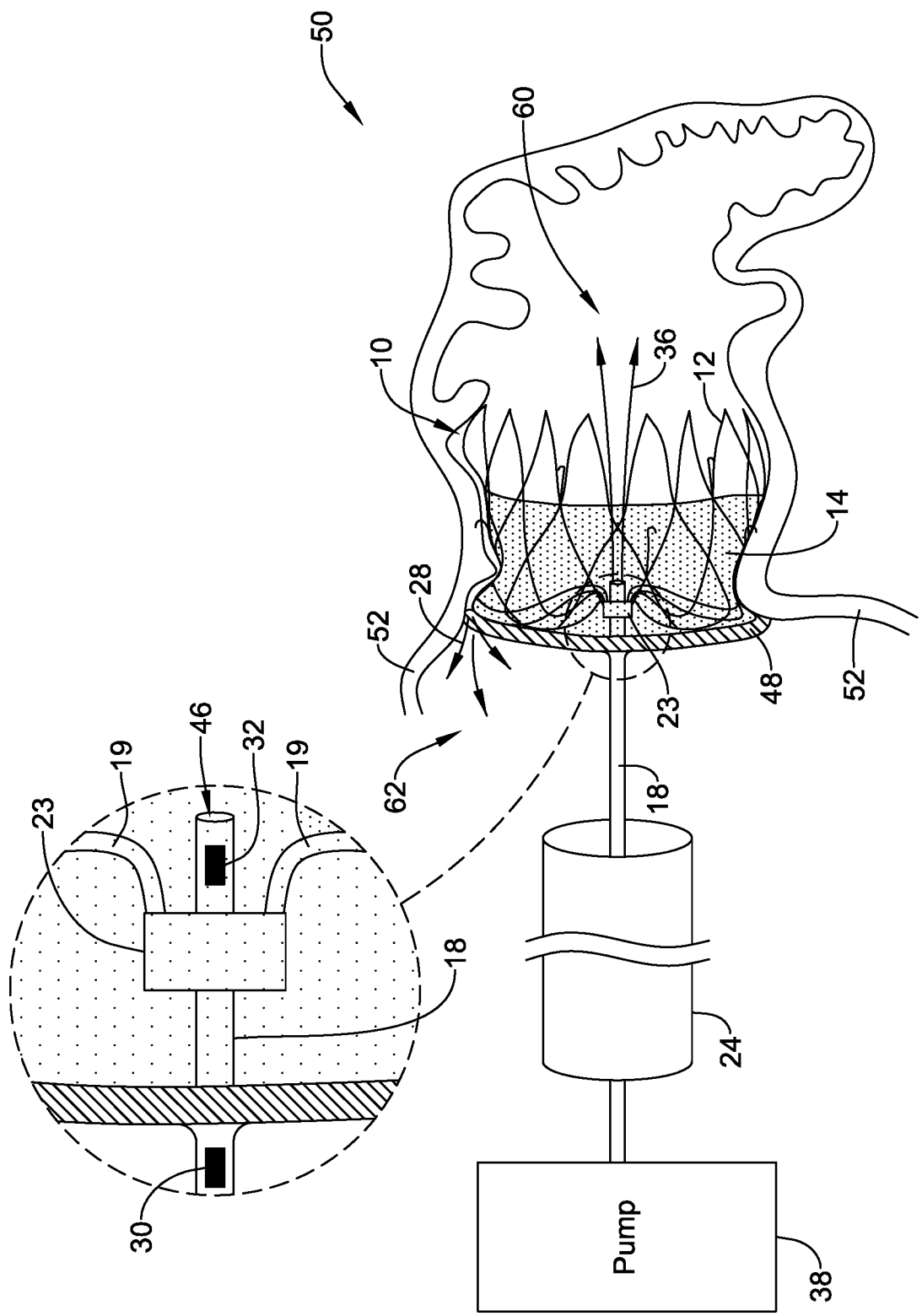
FIG. 8 illustrates a portion of another occlusive member sensing system.

FIG. 8 illustrates another example of a system and methodology to detect leakage around an example occlusive implant 10. FIG. 8 shows the occlusive implant 10 positioned within the opening of the left atrial appendage 50 similarly to that described above. Similarly to that described above with respect to FIG. 5, FIG. 8 illustrates that the example occlusive implant 10 may be coupled to a core wire 18. The core wire 18 may be coupled to a pump 38. Additionally, as illustrated in the detailed view of FIG. 8, the core wire 18 may be attached to the occlusive implant 10 via the central the hub 23. Further, the detailed view of FIG. 8 illustrates the support members 19 of the framework 12 attached to the central hub 23. The detailed view of FIG. 8 further illustrates a first sensor 30 positioned along a portion of the core wire 18. Additionally, the detailed view of FIG. 8 further illustrates a second sensor 32 disposed along a portion of the core wire 18 adjacent to the central hub 23. It should be noted that in some examples, the core wire 18 is attached to the central hub 23.

FIG. 8 further illustrates that, in some examples, a membrane 48 may be coupled to the core wire 18. The membrane 48 may extend along the outer surface of the framework 12, whereby the membrane is designed to prevent fluid from leaking out of the occlusive implant 10. In other words, in instances where the occlusive member 14 is porous, the membrane 48 may be utilized to maintain a level of pressure within the occlusive implant 10 while fluid leakage is detected via any of the methodologies described above. In some examples, the membrane 48 may be coated with a dissolvable wax, gel, sugar, salt or other similar media or compound to tailor the porosity of the membrane 48 and/or occlusive member 14. This coating may be designed to dissolve on its own or in accordance with a thermal or chemical means during and/or after leakage detection has taken place.

For example, FIG. 8 illustrates that in some instances the core wire 18 may include a lumen 46 through which fluid may be pumped. FIG. 8 further illustrates that the distal end region of the core wire 18 may extend through the occlusive implant 10 such that the distal end region of the core wire 18 may be positioned inside the left atrial appendage 50. Further, FIG. 8 illustrates that fluid 36 may be pumped through the lumen 46 of the core wire 18 into the inside portion 60 of the left atrial appendage 50. The membrane may be held in place while the fluid 36 is pumped into the left atrial appendage 50. Additionally, FIG. 8 shows fluid 28 leaking from one side of the occlusive implant 10 (e.g., from the inside area 60) to the other side of the occlusive implant 10 (e.g., to an area 62 within the left atrium).

As described above, it can be appreciated that the first sensor 30 may be utilized to measure a first parameter (e.g., a first fluid flowrate, a first fluid pressure, etc.) on the outside of the occlusive implant 10, while the second sensor 32 may be utilized to measure a second parameter (e.g., a second fluid flowrate, a second fluid pressure, etc.) on the inside of the occlusive implant 10. As discussed above, comparison of the parameter measurements (or parameters calculated based upon the collected first parameter and the second parameter) may be utilized to determine the presence and extent of fluid leakage around the occlusive implant 10. Additionally, it is contemplated that the membrane 48 may be retracted/removed after the first parameter and second parameters are determined.

Figure 9:
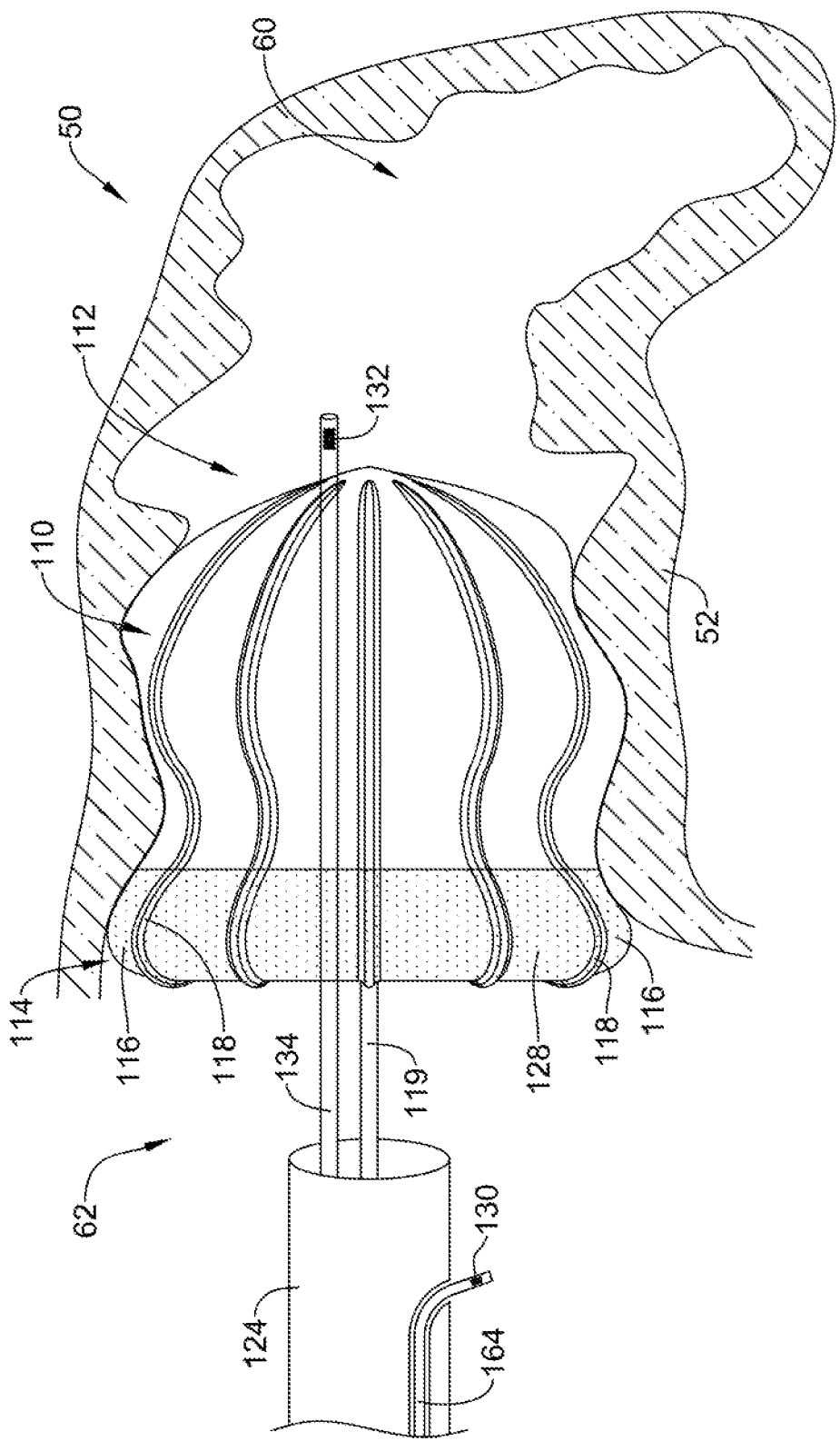
FIG. 9 illustrates another occlusive member sensing system.

FIG. 9 illustrates another example occlusive implant 110 positioned an opening of the left atrial appendage 50. Further, FIG. 9 illustrates another example of a system and methodology to detect leakage around an example occlusive implant 110. The occlusive implant 110 may be configured to shift between a collapsed configuration and an expanded configuration. For example, in some instances, the occlusive implant 110 may be in a collapsed configuration during delivery via an occlusive device delivery system, whereby the occlusive implant 110 expands to an expanded configuration once deployed from the occlusion implant delivery system.

FIG. 9 further illustrates that the occlusive implant 110 may include a first end region 112 and a second end region 114. As will be discussed in greater detail below, the first end region 112 may include the portion of the occlusive implant 110 which extends farthest into a left atrial appendage 50, while the second end region 114 may include the portion of the occlusive implant 110 which is positioned closer to an opening of the left atrial appendage 50.

The occlusive implant 110 may include an expandable member 116. The expandable member 116 may also be referred to as an expandable balloon 116. The expandable member 116 may be formed from a highly compliant material (e.g., "inflation material") which permits the expandable member 116 to expand from a first unexpanded (e.g., deflated, collapsed, delivery) configuration to a second expanded (e.g., inflated, delivered) configuration. In some examples, the expandable member 116 may be inflated to pressures from about 1 psi to about 200 psi. It can be appreciated that the outer diameter of the occlusive implant 110 may be larger in the expanded configuration versus the unexpanded configuration. Example materials used for the inflation material may be hydrogel beads (or other semi-solid materials), saline, etc.

In some examples, the expandable member 116 may be constructed from silicone or a low-durometer polymer, however, other materials are contemplated. Additionally, the expandable member 116 may be impermeable to blood and/or other fluids, such as water. In some embodiments, the expandable member 116 may include a woven, braided and/or knitted material, a fiber, a sheet-like material, a metallic or polymeric mesh, or other suitable construction. Further, in some embodiments, the expandable member 116 may prevent thrombi (e.g., blood clots, etc.) originating in the left atrial appendage from passing through the occlusive implant 110 and into the blood stream. In some embodiments, the occlusive implant 110 may promote endothelial growth after implantation, thereby effectively removing the left atrial appendage from the patient's circulatory system. Some suitable, but non-limiting, examples of materials for the occlusive implant 110 are discussed below.

FIG. 9 further illustrates that occlusive implant 110 may include one or more spine members 118 extending along the expandable member 116 from the second end region 114 to the first end region 112. In some examples described herein, the spine members 118 may be described as positioning members 118. FIG. 9 further illustrates that the each of the individual spine members 118 may be spaced apart from adjacent spine members 118. In other words, the spacing between adjacent spine members 118 may be substantially uniform around the circumference of the expandable member 116. In some examples, the spine members 118 may include one or more materials which are stiffer, higher durometer materials than the material utilized to construct the expandable member 116. Some suitable, but non-limiting, examples of materials for the spine members 118 are discussed below.

FIG. 9 further illustrates that the occlusive implant 110 may include a coating 128. The coating 128 may extend around the circumference of the occlusive implant 110 (including both the expandable member 116 and the spine members 118). In some examples, the coating 128 may promote cellular growth along the surface thereof. For example, the coating 128 may include elements which promote endothelial growth along the surface thereof. For example, the endothelial growth elements may accelerate the ability for endothelial cellular tissue to form a seal across an opening of the left atrial appendage. In other examples, the coating 128 may include a polymer mesh (e.g., PET mesh), a woven, braided and/or knitted material, a fiber, a sheet-like material, a metallic or polymeric mesh, or other similar materials which may be coupled to the outer surface of the expandable member 116.

Additionally, FIG. 9 illustrates that the example occlusive implant 110 may be coupled to a core wire 119. Further, FIG. 9 illustrates that both the core wire 119 and a catheter 134 may extend through a delivery catheter 124. FIG. 9 also illustrates that the catheter 134 may extend along the occlusive implant 110 such that the distal end region of the catheter 134 may be positioned inside the left atrial appendage 50.

Additionally, FIG. 9 illustrates that a second catheter 164 may extend along the delivery catheter 124. For example, the delivery catheter 124 may include a second lumen through which the second catheter 164 may extend. Further, FIG. 9 illustrates that a first sensor 130 may be positioned along the catheter 164 at a location which is outside of the occlusive implant 110. Additionally, FIG. 9 shows that, in some examples, a second sensor 132 may be positioned along the distal end region of the catheter 134.

Similarly to that discussed above, it can be appreciated that the first sensor 130 (e.g., a first thermocouple) may be utilized to measure a first parameter (e.g., a first fluid temperature, a first fluid flowrate, a first fluid pressure, etc.) on the outside (e.g., from the area 62 within the left atrium) of the occlusive implant 110, while the second sensor 132 (e.g., a second thermocouple) may be utilized to measure a second parameter (e.g., a second fluid temperature, a second fluid flowrate, a second fluid pressure, etc.) on the inside (e.g., from the inside area 60) of the occlusive implant 110.

As discussed above, comparison of the parameter measurements (or parameters calculated based upon the collected first parameter and the second parameter) may be utilized to determine the presence and extent of fluid leakage around the occlusive implant 110.

The materials that can be used for the various components of the occlusive implant 10 and/or occlusive implant 110 (and variations, systems or components thereof disclosed herein) and the various elements thereof disclosed herein may include those commonly associated with medical devices. For simplicity purposes, the following discussion makes reference to the occlusive implant 10 and/or occlusive implant 110 (and variations, systems or components disclosed herein). However, this is not intended to limit the devices and methods described herein, as the discussion may be applied to other elements, members, components, or devices disclosed herein.

In some embodiments, the occlusive implant 10 and/or occlusive implant 110 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC), dynamic mechanical thermal analysis (DMTA) analysis over a large temperature range and bend and free recovery (ASTM F2082). For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 and/or occlusive implant 110 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 and/or occlusive implant 110 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 and/or occlusive implant 110 (and variations, systems or components thereof disclosed herein) to achieve the same result.

In some embodiments, a degree of Magnetic Resonance Imaging (MM) compatibility is imparted into the occlusive implant 10 and/or occlusive implant 110 (and variations, systems or components thereof disclosed herein). For example, the occlusive implant 10 and/or occlusive implant 110 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 and/or occlusive implant 110 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 and/or occlusive implant 110 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 and/or occlusive implant 110 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A system for detecting leakage around an occlusive implant disposed in a left atrial appendage, the system comprising:
    an occlusive implant;
    an elongate shaft having a port disposed at a distal end region thereof; and
    a first sensor disposed adjacent the elongate shaft;
    wherein the elongate shaft is configured to be positioned adjacent the occlusive implant such that the first sensor is positioned on a first side of the occlusive implant, and wherein the port is positioned on a second side of the occlusive implant;
    wherein the first sensor is configured to measure a first parameter;
    wherein the first parameter is utilized to determine a fluid leak between the occlusive implant and a tissue wall defining the left atrial appendage,
        further comprising a retractable membrane that includes an absorbable material configured to prevent fluid from passing therethrough coupled to the first side of the occlusive implant, and
    wherein the elongate shaft further includes a fluid pump operably coupled to a proximal end region of the elongate shaft.

2. The system of claim 1, wherein the first parameter includes at least one of a fluid flowrate, a fluid pressure and a fluid temperature.

3. The system of claim 1, wherein the elongate shaft is configured to inject fluid into the left atrial appendage.

4. The system of claim 1, wherein the elongate shaft includes a core wire and a second sensor, wherein the core wire is coupled to the occlusive implant, and wherein the first sensor is disposed on the core wire on the first side of the occlusive implant, and wherein the second sensor is disposed on the core wire on the second side of the occlusive implant.

5. The system of claim 1, wherein the first sensor is wireless.

6. A system for detecting leakage around an occlusive implant disposed in a left atrial appendage, the system comprising:
    an occlusive implant;
    an elongate shaft having a first sensor disposed on a first portion thereof and a second sensor disposed along a second portion thereof;
    wherein the elongate shaft is configured to be positioned adjacent the occlusive implant such that the first sensor is positioned on a first side of the occlusive implant, and wherein the second sensor is positioned on a second side of the occlusive implant;
    wherein the first sensor is configured to measure a first parameter;
    wherein the second sensor is configured to measure a second parameter;
    wherein the first parameter is compared to the second parameter to determine a fluid leak between the occlusive implant and a tissue wall defining the left atrial appendage, further comprising a retractable membrane that includes an absorbable material configured to prevent fluid from passing therethrough coupled to the first side of the occlusive implant, and wherein the elongate shaft further includes a fluid pump operably coupled to a proximal end region of the elongate shaft.

7. The system of claim 6, wherein the first parameter, the second parameter or both the first parameter and the second parameter include at least one of a fluid flowrate, a fluid pressure and a fluid temperature.

8. The system of claim 6, wherein the elongate shaft is operably coupled to a hub on the occlusive implant.

9. The system of claim 6, further comprising a core wire releasably coupled to the occlusive implant.

10. The system of claim 6, wherein the first sensor, the second sensor or both the first and second sensor are wireless.

11. The system of claim 1, wherein the elongate shaft is configured to vacuum fluid out of the left atrial appendage.

12. The system of claim 1, further comprising a core wire releasably coupled to the occlusive implant, and wherein the first sensor is disposed on the core wire.

13. The system of claim 12, further comprising a second sensor disposed on a hub of the occlusive implant.

14. The system of claim 1, wherein the first sensor is attached to the elongate shaft.

15. The system of claim 14, further comprising a second sensor attached to the elongate shaft on the second side of the occlusive implant.

\* \* \* \* \*